United States Patent [19]

Wagner et al.

[11] Patent Number: 5,234,820

[45] Date of Patent: Aug. 10, 1993

[54] EXOPEPTIDASE CATALYZED SITE-SPECIFIC BONDING OF SUPPORTS, LABELS AND BIOACTIVE AGENTS TO PROTEINS

[75] Inventors: Fred W. Wagner, Walton, Nebr.; Thomas R. Coolidge, Falls Village, Conn.; Sheldon M. Schuster, Gainesville, Fla.; Jay Stout; Dwane E. Wylie, both of Lincoln, Nebr.; Klaus Breddam, Glostrup, Denmark; William Lewis, Lincoln, Nebr.

[73] Assignees: Board of Regents of the University of Nebraska; BioNebraska, Inc., both of Lincoln, Nebr.

[21] Appl. No.: 545,915

[22] Filed: Jun. 28, 1990

Related U.S. Application Data

[63] Continuation-in-part of Ser. No. 375,138, Jun. 30, 1989.

[51] Int. Cl.$^5$ .................... C12P 1/00; G01N 33/532; G01N 33/547; C12N 11/06
[52] U.S. Cl. ........................ 435/41; 435/7.1; 435/7.92; 435/181; 436/532; 436/544; 530/816
[58] Field of Search ................ 435/41, 174, 177, 181, 435/7.1, 7.92; 436/532, 544; 530/816

[56] References Cited

FOREIGN PATENT DOCUMENTS 0085516 1/1981 European Pat. Off. .

OTHER PUBLICATIONS

Kauer, et al., The Journal of Biological Chemistry. vol. 261, No. 23, 1986, pp. 10695-10700.

*Primary Examiner*—David M. Naff
*Attorney, Agent, or Firm*—Merchant, Gould, Smith, Edell, Welter & Schmidt

[57] ABSTRACT

An auxiliary substance such as a label, support, or bioactive agent is attached to a protein at a site that is remote from the active site of the protein by the use of exopeptidase and a nucleophile which is an amino acid, amino acid derivative, amine or alcohol. In one embodiment, the nucleophile is attached to the carboxy terminus of a protein by catalysis with exopeptidase to form an adduct and then the adduct or its combination with a linker arm is bound to the auxiliary substance. In another embodiment, the auxiliary substance or its combination with a linker arm is bound to the nucleophile to form an intermediate substance which is then coupled by catalysis with exopeptidase to the carboxy terminus of a protein.

7 Claims, 2 Drawing Sheets

EXOPEPTIDASE CATALYZED SITE-SPECIFIC BONDING OF SUPPORTS, LABELS AND BIOACTIVE AGENTS TO PROTEINS

CROSS-REFERENCE TO RELATED APPLICATION

This application is a continuation-in-part of U.S. patent application Ser. No. 07/375,138, filed Jun. 30, 1989.

TECHNICAL FIELD

This invention relates to immobilized and labeled proteins and to the attachment of proteins to bioactive agents. Specifically, it relates to methods for attaching labels, immobilization supports and bioactive agents to specific sites of proteins.

BACKGROUND OF THE INVENTION

It is well-known that the function of bioactive proteins can often be enhanced by their combination with other substances. When used to catalyze a reaction or to obtain separation, proteins can be immobilized to increase reaction efficiency and simplify the processing. When used as detecting agents, proteins can be labeled to facilitate measurement. When used to complex with or treat biological organisms, proteins can be combined with bioactive agents (hereinafter called "augmentation") to help achieve treatment efficacy.

Methods for immobilizing proteins are desirable because they localize reaction sites and improve economic recovery. Moreover, immobilized proteins are generally less susceptible to the loss of activity due to chemical attack and changes in temperature and pH than are free proteins.

Methods for labeling or augmenting proteins are desirable because they facilitate quantification, localization, specificity and reactivity of the protein. The resulting combinations, moreover, are the resulting combinations and/or powerful tools for clinical analysis and treatment.

Numerous techniques exist for protein immobilization on solid supports. Proteins can be physically adsorbed onto inert supports or can be covalently bound to the support through reaction with bifunctional linker arms. Microencapsulation, gel entrapment and complexation (with ion exchange resins) also can bind and immobilize.

Numerous techniques also exist for binding labels and bioactive agents to proteins. Most of these techniques call for reaction of the label or agent and a functional group of the protein, such as an amino group, which occurs repeatedly throughout the protein. Although some repetitions of such a group are shielded from binding by the conformation of the protein, many others are exposed and available for binding with the labeling group or bioactive agent. The result is a mixture of proteins having labels or bioactive agents attached at various nonspecific sites.

With any of these techniques for immobilizing, labeling or augmenting, several criteria should be met. The first is a correct spatial orientation for optimum reactivity of the proteins. A protein functions best when it is bound in a fashion that orients its active sites away from the support, label or bioactive agent and renders the sites available for functional operation. The second is the exhibition of protein activities and specificities that are at least comparable to those exhibited by the unbound form of the protein. The third, which is especially applicable to immobilization, is the capability for repeated use and for a high packing density. The fourth is the avoidance of attachment of the support, label or agent within or in the vicinity of the active site of the protein. Otherwise, the resulting loss of functional capacity often causes inadequate reactivity and the need to use more protein.

One of the most important protein embodiments being investigated today is the antibody. The need to minimize the attachment of immobilizing supports, labeling groups or bioactive agents within or near the antigen-binding site of an antibody is widely recognized.

One method for such minimization involves binding antigen to the antibody prior to reaction with the labeling group, bioactive agent, or immobilizing support. In this manner, the antigen shields the antibody binding site from reaction. The success of this shielding method, however, is limited. Although a high affinity of the antibody for the antigen exists, the equilibrium between the antibody/antigen complex and the free antibody/antigen enables free antibody to react. This has foreseeable negative consequences. In addition, exposure of the antigen to a labeling group, bioactive agent, or immobilizing support often results in attachment of that material to the antigen.

The known methods for immobilizing, labeling or augmenting any kind of protein fall far short of maintaining the functional capacity of the protein. Protein reactivity is generally lessened. Proper spatial orientation and packing density are often lacking. And, as a result, many attendant economic, toxic, reactive and non-specificity problems occur. Consequently, better and more specific methods for binding labels, supports or bioactive agents to proteins are needed.

It is an object of the invention, therefore, to develop methods for labeling, immobilizing or bioactively augmenting proteins at sites remote from the functionally active site or sites of the protein. It is also an object of the invention to immobilize proteins by covalently binding them to an inert immobilization support. Another object of the invention is to covalently bind a label to a specific site of a protein. Another object is to covalently bind bioactive agents to a specific location on a protein. A further object of the invention is to immobilize proteins so that they have the correct spatial orientation and packing density which will allow unhindered access to the functionally active site.

SUMMARY OF THE INVENTION

These and other objects are achieved by the present invention which is directed to methods for immobilizing, labeling and augmenting proteins. Generally, the method involves binding the immobilization support, label or bioactive agent (hereinafter called "auxiliary substance") to a protein at a specific site so that interference with the function and performance of the protein is minimized or eliminated. Preferably, this specific site is highly remote from the active sites of the protein.

In particular, the method of the invention involves two primary reactions. The first (hereinafter called the "primary coupling reaction"), catalytically couples an amino acid, an amino acid derivative, an amine or an alcohol (hereinafter called "nucleophile"), to the carboxy terminus of the protein through the use of an exopeptidase enzyme. The second (hereinafter called the "primary binding reaction"), binds the side chain of the nucleophile to a specifically reactive group attached to the auxiliary substance.

The method of the invention can be practiced by alternative synthetic routes depending on whether the primary coupling reaction or primary binding reaction is conducted first. These two routes are depicted in the scheme presented in the following section entitled Detailed Description of the Invention.

The first synthetic route can be employed with all sizes and solubilities of reactants. A nucleophile having a distinctive side chain is first coupled to the carboxy or carboxy ester terminus of the protein by the primary coupling reaction. This coupling either adds the nucleophile to the carboxy terminus of the protein (condensation) or substitutes the nucleophile for the amino acid residue forming that carboxy terminus (transpeptidation with amino acid or amine or transesterification with alcohol) or substitutes the nucleophile for the alcohol group of a terminal amino acid ester residue. The resulting protein-nucleophile adduct is then bound to an auxiliary substance by the primary binding reaction which takes advantage of the distinctive character of the side chain. The adduct either is directly bound to the auxiliary substance or is indirectly bound through a bifunctional linker arm. In either case, the binding reaction occurs between the side chain of the nucleophile and a specifically reactive group on the auxiliary substance or linker arm.

The second synthetic route can be employed when the molarities of the reactants in the reaction medium are sufficient to permit relatively rapid enzymatic coupling. A nucleophile is first bound to the auxiliary substance by the primary binding reaction to form an intermediate of the auxiliary substance and nucleophile. The binding can be accomplished by direct reaction of the side chain of the nucleophile and the auxiliary substance or indirectly through a linker arm that has been prebound to the auxiliary substance. The intermediate is then coupled to the carboxy terminus of the protein by the primary coupling reaction. Transpeptidation, condensation and transesterification with amino acid, amino acid derivatives, amine or alcohol nucleophiles can all be employed in this primary coupling reaction.

The proteins used in the method of the invention are biologically-active polypeptides. Included without limitation are enzymes, enzyme inhibitors, peptide hormones, DNA binding proteins, reading frame proteins, transcriptases, antibodies, $F_{ab}$ truncated antibodies, antibody fragments, regulating proteins, peptides as small as two residues and various other functional proteins.

The preferred proteins for use in the inventive method are monoclonal or polyclonal antibodies. Preferred classes of antibodies include those that function to detect antigens in biological systems or contaminants in biological or inanimate systems, to carry bioactive agents to specific sites, to diagnose disease and organic disfunction, to separate antigens from other materials in biological or inanimate systems, and to remove antigens from biological or inanimate systems. Especially preferred embodiments are mammalian immunoglobulin proteins from the IgA, IgD, IgE, IgM, or IgG class of immunoproteins.

The amino acid nucleophile used in the method of the invention is an alpha amino acid or amino acid derivative having a side chain with a reactive substituent. Alternatively, it may have a simple, nonfunctional side chain in circumstances where it is also the auxiliary substance. When the first synthetic route is employed, the side chain is chosen so that the amino acid nucleophile has a distinctive character relative to the amino acids of the protein. With this design, the amino acid nucleophile rather than the amino acids of the protein is selectively and preferentially reacted with a specifically reactive group of the linker arm or auxiliary substance. When the second synthetic route is employed, such a distinctive character can be used but is not necessary because the primary coupling reaction provides the selectivity desired.

The amine nucleophile used in the method of the invention mimics the amino acid nucleophile. It is a $C_2$ to $C_{20}$ aliphatic, aromatic or arylaliphatic primary amine having a reactive substituent along its backbone or at its other terminus. The foregoing conditions regarding the character of the amino acid side chain also apply when an amine is employed in the first and second synthetic routes.

The alcohol nucleophile used in the method of the invention is an aliphatic, aromatic or arylaliphatic $C_1$ to $C_{20}$ primary alcohol having a reactive substituent along its backbone or at its other terminus.

The linker arm used in the method of the invention is a flexible or semi-flexible chain which has as its termini (1) a specifically reactive group that is reactive with the side chain of the nucleophile and (2) an other functional group that reacts with a combining group of the auxiliary substance.

Immobilizing supports useful in the present invention are inorganic or organic materials which may be functionalized with a specifically reactive group for selective reaction with the side chain of the nucleophile, or with a combining group that reacts with the other functional group of the linker arm. The support is a porous or semiporous material that is biologically inert and insoluble in the medium used.

Bioactive agents include those that act to provide a desirable biochemical or therapeutic result. They may be functionalized with a specifically reactive group for reaction with the side chain of the nucleophile, or with a combining group that reacts with the other functional group of the linker arm. Included are chemotherapeutic agents, oxidizing or reducing agents, cytotoxic agents, anticancer agents, radioactive agents, antibiotics, antimicotics, anti-infectives, heavy metal agents, antiviral agents, lysing agents, chelating groups and the like.

Labels useful in the present invention include fluorescent groups, phosphorescent groups, colorimetric groups, radioactive groups, luminescent groups, spectrometric groups nuclear magnetic resonance groups, electron spin resonance groups and other groups with physiochemical properties that may be detected by measuring means. These labels may be functionalized with a specifically reactive group for reaction with the side chain of the nucleophile, or with a combining group that is reactive toward the other functional group of the linker arm. The nucleophile may also function as a label when it carries radioactive atoms.

The enzymes that carry out the primary coupling reactions are exopeptidases. They act specifically at the C-terminal end of peptide chains to form or transform peptide bonds under basic conditions (condensation and transpeptidation) or acidic conditions (transesterification) and are relatively stable under the reaction conditions used.

Preferred groups of exopeptidases for the method of the invention are serine carboxypeptidases. Certain of these enzymes, known as carboxypeptidase Y, are specific for amino acids, or amines with neutral or basic side chains. Certain other classes of carboxypeptidase enzymes are specific for amino acids with acidic side chains. Correlation of the exopeptidase enzyme specificity and the neutral, acidic or basic character of the nucleophile to be coupled to the protein is appropriate according to the method of the invention.

The conditions for the enzymatically catalyzed reaction between the protein and the nucleophile include control of pH, temperature, concentration and incubation time.

The present invention is also directed to methods which employ the labeled, immobilized or augmented protein.

The method for use of the labeled protein involves combining of the labeled protein and the material upon which it is to act, removing any excess labeled protein and measuring the amount of labeled protein that has interacted with the material. In particular, this method is useful for detection of antigens or enzymatic substrates/inhibitors by antibodies or enzymes, respectively.

The method for use of immobilized protein proceeds in a known manner as indicated by the character of the protein. The protein preferably is an enzyme, antibody, DNA binding protein or regulatory protein. The preferred uses will include enzymatically catalyzed reactions, antibody-antigen complexations, regulation of reactions and DNA or enzyme separations and/or purifications. One advantage of this method is the increased efficiency and ease of removal of the immobilized protein due to the immobilization at a specific and constant site remote from the reactive sites. Another advantage is the ability to increase the packing density of the immobilized protein when all molecules are aligned in the same direction and have exposed active sites.

The method for use of a bioactive agent bound to a protein also proceeds in a recognized manner as indicated by the bioactive agent and the nature of the protein. The action of the protein and bioactive agent cooperate to cause the effect desired. The protein may act as a carrier to transport the agent across membranes or to cause its absorption into fluids, media or cells. It may also act as an absorption inhibitor to prevent transport of the agent across membranes or to prevent its absorption into fluids, media or cells. It may further act as a targeting vehicle to direct the agent to selective tissue sites or receptors. The advantage of this method is that by leaving the active sites free, the reaction efficiency and tissue selection are increased.

In sum, the present invention is directed to methods for forming a protein bound to an auxiliary substance. One such method comprises the steps of (a) coupling a nucleophile to the protein by catalysis with an exopeptidase enzyme to form an adduct, wherein the nucleophile is an amino acid, amino acid derivative, amine or alcohol having a side chain with a distinctive reactive substituent, and (b) binding the adduct to the auxiliary substance or its combination with a linker arm to form the bound protein, the auxiliary substance or combination having a specifically reactive group that is correlatively reactive toward the distinctive reactive substituent of the adduct. Another method of binding a protein to an auxiliary substance includes the steps of (a) binding a nucleophile to the auxiliary substance or its combination with a linker arm to form an intermediate, wherein the nucleophile is an amino acid, amino acid derivative, amine or alcohol having a side chain with a reactive substituent and the auxiliary substance or combination has a reactive group that is reactive toward the reactive substituent of the nucleophile, and (b) coupling the intermediate to the protein by non-neutral catalysis with an exopeptidase enzyme to form the bound protein.

According to either of these two methods, the auxiliary substance may be an immobilization support, a label or a bioactive agent. It is preferred that the methods employ the combination of the auxiliary substance covalently bound to the linker arm having the specifically reactive functional group terminating the free end of the linker arm. Under basic catalysis conditions, it is preferred that the nucleophile is an amino acid, amino acid derivative or amine. Under acidic catalysis conditions, it is preferred that the nucleophile is an alcohol. It is further preferred that catalysis conditions include a rapid incubation time. Amino acid nucleophiles may include aliphatic amino acids, hydroxy amino acids, sulfur-containing amino acids, diamino monocarboxylic acids, aromatic amino acids, heterocyclic amino acids, and activated derivatives thereof. It is preferred that the amino acid nucleophile is serine, taurine, or alanine.

The protein in either method may be an antibody, an enzyme, an enzyme inhibitor, a protein hormone, a DNA binding protein, a regulatory protein or a DNA reading frame protein. It is preferred that the protein is a monoclonal or polyclonal antibody, and that the nucleophile is substantially completely bonded to the carboxyl terminus of the heavy chain of the antibody. It is also preferred that the protein is an IgG immunoprotein.

The exopeptidase enzyme may be a carboxypeptidase, preferably a serine or cysteine carboxypeptidase.

The invention is also directed to methods for preparing a labeled protein. The methods comprise coupling a protein and a nucleophile of a labeled amino acid, amino acid derivative, amine or alcohol in a nonneutral medium and in the presence of an exopeptidase enzyme. The label may be fluorescent, nuclear magnetic, phosphorescent, colorimetric, magnetic, electron resonant or spectrometric. One particular method according to the invention comprises (a) coupling a protein and a nucleophile in a non-neutral medium and in the presence of an exopeptidase enzyme to form an adduct, the nucleophile having a side chain with a distinctive reactive substituent preferably selected from the group consisting of sulfhydryl, hydroxyl, activated hydroxyl, olefinyl, activated ester, amino, azidyl, hydrazinyl, phosphoramidoyl, boronyl, ferrocenyl, ferro complexes and any mixtures thereof, (b) combining a label and a linker arm to form a combination, the label having at least one reactive group and the linker arm being a flexible or semi-flexible chain having a specifically reactive group that is correlatively reactive with the distinctive reactive substituent and another functional group that is reactive toward the reactive group of the label, and (c) binding the adduct and the combination to form the labeled protein. Another labeling method comprises (a) combining a label and a linker arm to form a combination, the label having at least one combining group, and the linker arm being a flexible or semi-flexible chain having a specifically reactive group that is or is rendered nonreactive with the combining group of the label and an other functional group that is reactive toward the combining group of the label, (b) binding the combination and a nucleophile to form an intermediate, the nucleophile having a side chain with a reactive substituent that is reactive toward the specifically reactive group of the combination, and (c) coupling a protein and the intermediate in a non-neutral medium and in the presence of an exopeptidase enzyme to form the labeled protein. Yet another method for preparing a labeled protein comprises (a) binding a label and a nucleophile to form an intermediate, the nucleophile having a side chain with a reactive substituent, and the label having a reactive group that is reactive with the reactive substituent of the nucleophile, and (b) coupling a protein and the intermediate in a non-neutral medium and in the presence of an exopeptidase enzyme.

The resulting labeled proteins may include a protein having a labeled nucleophile of an amino acid, amino acid derivative, amine or alcohol coupled to or substituted on its carboxyl terminus. Preferably, the nucleophile is substantially exclusively coupled to or substituted on the carboxy terminus. It is preferred that the protein is a monoclonal or polyclonal antibody, and that the nucleophile is serine, taurine, or alanine. It is further preferred that the labeled nucleophile is radioactive.

In the protein labeling methods according to the invention, it is preferred that the protein concentration is about 1 μM to about 1 mM, and the enzyme concentration is from about 1 pM to mM. Under acidic coupling conditions, it is preferred that the nucleophile is an alcohol. Under basic coupling conditions, it is preferred that the nucleophile is an amino acid, amino acid derivative, or amine; that the coupling reaction is conducted for at least 5 seconds; and that the protein, nucleophile and enzyme are combined in an aqueous mixture. This mixture may be formed by (a) combining the protein and the nucleophile to form a mixture, (b) adjusting the pH of the mixture to within a range of about 2.0 to 10.5, and (c) adding the enzyme to the mixture.

The invention also provides a method for detecting the presence of an antigen. The method includes the steps of (a) combining a labeled antibody with a material suspected of containing an antigen to form a complex, the labeled antibody being specifically immunoreactive with the antigen, (b) removing any uncomplexed labeled antibody, and (c) measuring the amount of labeled antibody present in the complex.

The invention further provides methods for preparing an immobilized protein. One such method includes the steps of (a) coupling a protein and a nucleophile in a non-neutral medium and in the presence of an exopeptidase enzyme to form an adduct, and (b) binding the adduct and an immobilization support to form the immobilized protein, wherein the support has at least one specifically reactive group that is correlatively reactive toward the distinctive reactive substituent of the adduct. Another method comprises (a) coupling a protein and a nucleophile in a non-neutral medium and in the presence of a exopeptidase enzyme to form an adduct, (b) combining an immobilization support and a linker arm to form a covalently bound combination, wherein the immobilization support has at least one combining group, and the linker arm is a flexible or semi-flexible chain having a specifically reactive group that is correlatively reactive with the distinctive reactive substituent of the adduct and another functional group that is reactive toward the combining group of the support, and (c) binding the adduct and the combination to form the immobilized protein. According to either method, the nucleophile may be an amino acid, amino acid derivative, amine or alcohol having a side chain with a distinctive reactive substituent, for example, a sulfhydryl, hydroxyl, activated hydroxyl, amino, activated ester, olefinyl, azidyl, hydrazinyl, phosphoramidoyl, boronyl ferrocenyl, ferro complexes and any mixture thereof.

Another method for preparing an immobilized protein according to the invention comprises (a) combining an immobilization support and a linker arm to form a covalently bound combination, the support having at least one combining group, and the linker arm being a flexible or semi-flexible chain having a specifically reactive group that is or is rendered non-reactive with the combining group and an other functional group that is reactive toward the combining group of the support, (b) binding the combination and a nucleophile to form an intermediate, the nucleophile preferably being an amino acid, amino acid derivative, amine or alcohol having a side chain with a reactive substituent that is reactive toward the specifically reactive group of the combination, and (c) coupling the intermediate and a protein in a nonneutral medium and in the presence of a exopeptidase enzyme to form the immobilized protein. Yet another method comprises the steps of (a) binding a nucleophile and an immobilization support to form an intermediate, the nucleophile preferably being an amino acid, amino acid derivative, amine or alcohol having a side chain with a reactive substituent, and the immobilization support having at least one specifically reactive group that is reactive toward the reactive substituent of the nucleophile, and (b) coupling a protein and the intermediate in a non-neutral medium and in the presence of an exopeptidase enzyme to form the immobilized protein.

According to any of the methods for preparing an immobilized protein of the invention, it is preferred that the carboxyl terminus of the protein is coupled to the support. The support may be inorganic or organic. Further, the support may be porous or semi-porous microparticles, microbeads, beads, spheres, gel particles, fibers, platelets, sheets or particulate material.

The invention further provides methods for preparing a protein augmented by a bioactive agent. One such method comprises (a) coupling a protein and a nucleophile in a non-neutral medium and in the presence of an exopeptidase enzyme to form an adduct, and (b) binding the adduct and a bioactive agent to form the augmented protein, the bioactive agent having at least one specifically reactive group that is correlatively reactive toward the reactive substituent of the adduct. Another method comprises the steps of (a) coupling a protein and a nucleophile in a non-neutral medium and in the presence of a exopeptidase enzyme to form an adduct, and (b) combining a bioactive agent and a linker arm to form covalently bound combination, the bioactive agent having at least one combining group, and that the linker arm being a flexible or semi-flexible chain having a specifically reactive group that is correlatively reactive toward the reactive substituent of the adduct and an other reactive group that is reactive toward the combining group of the bioactive agent, and (c) binding the adduct and combination to form the augmented protein. Preferably, the nucleophile is an amino acid, amino acid derivative, amine or alcohol having a side chain with a distinctive reactive substituent selected from the group consisting of sulfhydryl, hydroxyl, activated hydroxyl, amino, activated ester, olefinyl, azidyl, hydrazinyl, phosphoramidoyl, boronyl ferrocenyl, ferro complexes and mixtures thereof, Another method for preparing a protein augmented by a bioactive agent includes (a) binding a nucleophile and a bioactive agent to form an intermediate, the nucleophile being an amino acid, amino acid derivative, amine or alcohol having a side chain with a reactive substituent, and the bioactive agent having at least one specifically reactive group that is reactive toward the reactive substituent of the nucleophile, and (b) coupling a protein and the intermediate in a non-neutral medium and in the presence of an exopeptodase enzyme to form the augmented protein. An alternative method of forming an augmented protein involves (a) combining a bioactive agent and a linker arm to form a covalently bound combination, the bioactive agent having at least one combining group, and that the linker arm being a flexible or semi-flexible chain having a specifically reactive group that is correlatively reactive toward the reactive substituent of the adduct and an other reactive group that is reactive toward the combining group of the bioactive agent, and (b) binding a nucleophile and the combination to form an intermediate, the nucleophile being an amino acid, amino acid derivative, amine or alcohol having a side chain with a reactive substituent that is reactive toward the specifically reactive group of the combination, and (c) coupling a protein and the intermediate in a non-neutral medium and in the presence of a exopeptidase enzyme.

According to methods for preparing an immobilized protein or for preparing a protein augmented by a bioactive agent, it is preferred that the nucleophile is an amino acid, amino acid derivative or amine under basic coupling conditions, and an alcohol under acidic coupling conditions.

The invention also includes methods for functionally reacting a protein by employing an immobilized protein as produced according to the methods of the invention. Further included are methods for conducting a bioreaction with a bioactive agent by employing a protein carrying a bioactive agent as produced according to the methods of the invention.

According to the methods of the invention, it is preferred that the "distinctive reactive substituent" and "specifically reactive group" are selected from the following pairs: (a) a sulfhydryl group and a organometallic group, (b) an olefinyl group and a dienyl group, (c) a polar olefinic group and its corresponding monomer or substituted forms thereof, (d) an affinity complexing compound and its substrate, (e) a pair of hydroborated olefinic groups, (f) an aromatic amino group and an epoxy activated ester or aldehyde group, (g) an azidyl or hydrazinyl group and an aromatic amino group, (h) an aromatic alcohol and an activated ester group, and (i) a hydrazine and a reducing sugar group.

It is also preferred according to the methods of the invention that the linker arm chain is a polymer or oligomer of amide, ester, carbonate, urethane, ether, glycidyl, olefin or hydrocarbon groups, or an aliphatic group of from about 2 to 20 atoms, or an aromatic group of from about 1 to 5 rings.

DETAILED DESCRIPTION OF THE INVENTION

Figure 1A:
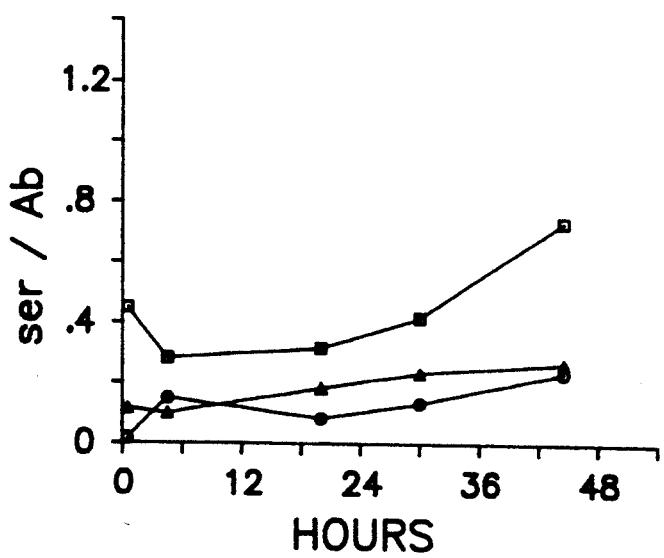
FIG. 1A is a graph of the pH dependence of the incorporation of serine in an antibody with respect to time at 0° C.

Until the present invention, a general method for highly selective, single site attachment of a auxiliary substance to a protein did not exist. The present methods solve this problem by providing precise control of the protein site to which the auxiliary substance is bound. This control causes the auxiliary substance to bind to a specific site on the protein that is as distant from the protein functional sites as possible, i.e. the carboxyl terminus.

More specifically, the present invention is based upon the discovery that amino acids, amino acid derivatives, amines and alcohols can be coupled to the carboxyl termini of biologically active proteins by a condensation or transpeptidation reaction under basic, exopeptidase catalysis conditions or by a transesterification reaction under acidic exopeptidase catalysis conditions (the primary coupling reaction). See J.S. Fruton in "Advances in Enzymology", A. Meister, ed. Vol. 53, 1982, John Wiley & Sons New York, pp. 239–306 for a general review of proteinase catalyzed synthesis of peptide bonds, the disclosure of which is incorporated herein by reference. With respect to almost all functional proteins, and especially antibodies, the carboxyl terminus of the peptide chain or chains occurs within a region of its three dimensional structure that is almost always remote from the active site region. In antibodies, for example, this terminus occurs within the constant region that is remote from the active, variable region of the antibody. Consequently, binding the auxiliary substance to the carboxy terminus of the protein provides the control sought.

As described in the foregoing Summary of the Invention, the attached substance is bound to the carboxy terminus of the protein through either of two synthetic routes. In the first, the nucleophile is separately coupled to the protein to form an adduct of the protein and nucleophile. The adduct is then bound to the auxiliary substance directly, or is bound indirectly through a linker arm-auxiliary substance combination.

In the second synthetic route, the nucleophile and auxiliary substance are directly bound, or indirectly bound through a linker arm, to form an intermediate. The intermediate is then coupled to the carboxy terminus of the protein.

These synthetic routes are depicted in the following scheme. Both synthetic routes operate in two versions, which depend upon whether the auxiliary substance is directly or indirectly bound to the nucleophile.

Scheme

Route 1

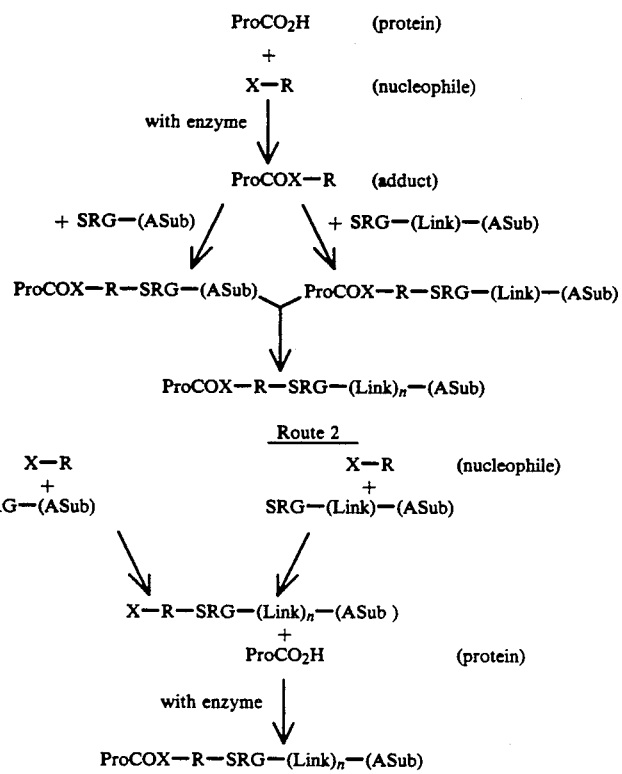

ProCO$_2$H is protein. R—X is the nucleophile, i.e., amino acid or aliphatic amine wherein R is the side chain and X is the attaching amine or hydroxy goup. ASub is attached substance. Link is a linker arm. SRG is specifically reactive group. The letter n is the number 0 and 1. Choice of X, R, SRG and route depend upon the functional groups of the protein and the solubilities of the reactants.

Route 1

According to route 1, the first step is the primary coupling reaction to form the adduct of protein and nucleophile. It is accomplished by exopeptidase catalysis under non-neutral conditions.

The choice of the particular amino acid, amino acid derivative, amine or alcohol as the nucleophile in the first step depends upon the identity of the amino acids of the protein and upon the distinctive character of the side chain of the nucleophile. The side chain of the coupled nucleophile acts as the binding site for the specifically reactive group of the attached substance or the combination of linker arm-attached substance. It has a structure that either is non-duplicative of the amino acids of the protein or is more highly reactive toward the specifically reactive group of the combination or auxiliary substance than are the amino acid side chains of the protein. It also is selected to avoid or minimize direct reaction with these side chains.

This selectivity imposed by the nucleophile side chain is accomplished by its reactive substituent. This substituent may be a sulfhydryl, olefinyl, amino, azidyl, hydrazinyl, epoxy, hydroxyl, activated hydroxy wherein the activator is a facile leaving group such as tosyl, mesyl and benzoyl, an acid group such as carboxyl, phosphoric or sulfonic, an activated ester such as a mixed anhydride, carbodiimido, iminyl amidinyl, imidazo, pivaloyl ester, neopentyl ester and the like, phosphoramidoyl, ferrocenyl, ferro complexes, boronyl and similar reactive functional groups.

In the second step of route 1, the primary binding reaction is accomplished by binding the nucleophile side chain either to the auxiliary substance or to its combination with the linker arm. In both of these variations, the specifically reactive group of the combination or auxiliary substance correlates with the reactive substituent of the side chain so that the side chain and auxiliary substance or combination readily react without substantially involving other groups of the protein.

To accomplish this selective reactivity of the primary binding reaction, the reactive substituent and specifically reactive group are correlated as pairs of groups. Several embodiments of this pair exhibit noncompetitive binding which essentially will not involve other groups of the protein. These include, for example:

(1) a sulfhydryl and an organometallic group, preferably an organomercuric group or Alman reagent which are particularly useful with antibodies because antibodies do not naturally contain free sulfhydryl groups, i.e. cysteine within or close to their active sites;

(2) an olefinyl group and a dienyl group, which form a Diels-Alder adduct;

(3) a phosphoramidoyl group and a metallophosphoramidoyl or metallophosphate group, which form co-ordinate complexes;

(4) an affinity complexing compound and its corresponding substrate, e.g. carbonic anhydrase and sulfanilamide or biotin and avidin, which form affinity complexes;

(5) a ferrocenyl group or ferro complex and a magnetic material rendered inert to the reaction medium, e.g. a teflon-coated iron wire coil, which form a magnetic couple;

(6) a chelating group and a chelated moiety such as ethylene diamine tetraacetate and a transition metal, which form a chelate;

(7) a polar olefinic or substituted olefinic group and the corresponding monomer, which polymerize by free-radical means under mild conditions, e.g. N-acryloyl lysine and acrylamide, and form a polymer;

(8) a pair of olefinic groups, which can be hydroborated and then treated with silver nitrate and weak base to form the reduced, coupled olefin-olefin adduct; and (9) a photoreactive arylketo group and a free radical stabilizing group having a radical-labile C—H bond; such as benzoylphenylalanine and a benzyl, allyl or arylalkyl group, which can be photolyzed to form an adduct between the keto carbon and the C—H carbon of the free radical stabilizing group. Preferably such free radical stabilizing groups as polyamide, polycinnamide, polystyrene, or fluorene containing polymers (supports), porphyrin or fluorescein, (label) and benzyl substituted bioactive agents are employed at significantly higher concentrations than the protein coupled to the arylketo nucleophile so that photolytic addition of the protein to itself is highly disfavored (See J.C. Kauer, et al., *J. Biol. Chem.*, 261, 10695 (1986)).

Other embodiments of this pair exhibit competitive binding relative to the functional groups of the protein but can be controlled to provide a substantially selective reaction of the side chain and attached substance or combination. These include, for example:

(1) an aromatic amino group and an epoxy, activated ester or aldehyde group, preferably an aromatic epoxy or aldehyde group, which can be reacted to form a nitrogen-carbon adduct, and under slightly acidic conditions to protonate the amine groups of the protein;

(2) an azidyl or hydrazinyl group and an aromatic amine, which can be reacted by irradiation with UV light to form a substituted amine, and under slightly acidic conditions to protonate the amine groups of the protein;

(3) an aromatic alcohol (e.g. phenolic group) or aromatic amine and an activated ester, which can be reacted to form an ester or amide respectively, and under slightly acidic conditions to protonate the amine groups of the protein; and (4) a hydrazine and a reducing sugar, which form an osazone.

The conditions and procedures for performing the binding reactions of the side chain and specifically reactive group are known in the art. See for example "Reagents for Organic Synthesis" by Fieser & Fieser, John Wiley & Sons, New York, Vol. I-X, 1967–1975, the disclosure of which is incorporated herein by reference.

The conditions will generally be approximately ambient temperatures (0 to 38 C), and dilute to moderate concentrations of reactants. The procedures will generally involve stirred reactors, removal of side products and slow addition of reagents. A further condition is the maintenance of a minimal concentration of any reactant that can react with more than one group in the reaction mixture. For example, a minimum concentration of auxiliary substance or combination in the binding reaction is to be maintained so that the chance of undesirable side reactions of the specifically reactive group with the protein are minimized.

Route 2

According to route 2, the nucleophile and the auxiliary substance or its combination with linker arm are first bound by the primary binding reaction to form an intermediate. This step can be accomplished by employing (1) any of the reactive substituent and specifically reactive group pairs described above; (2) the combining group and other functional group pairs described below for the linker arm, or (3) by any of the known methods for forming an amide, ester, ether, imino, carbonate, urethane (carbamate), carbon-carbon, carbon-nitrogen, sulfur-carbon, sulfur-oxygen-carbon or carbon-oxygen bond. Methods to form these bonds and the particular groups formed thereby are known in the art. See, for example "Chemical Reagents for Protein Modification", CRC Press Inc., R.L. Lundblad & C.M. Noyes ed. 1984; "Basic Principles of Organic Chemistry", J.D. Roberts and M. Caserio, Benjamin Press, 1975, the disclosures of which are incorporated herein by reference.

Choice of the particular manner of binding the auxiliary substance or combination to the nucleophile does not depend upon the structure of the protein according to this route. Any stable binding group that is appropriate for the chemical structures of nucleophile and auxiliary substance or linker arm combination will suffice because this binding reaction is not conducted in the presence of the protein.

The second step of route 2 couples the intermediate to the protein through the primary coupling reaction of the nucleophile portion of the intermediate and the protein carboxy terminus. It is accomplished by exopeptidase catalysis under non-neutral conditions. The selectivity of this reaction suits it as the one to be conducted in the presence of protein. The scheme of route 2 utilizes this feature to best advantage because it places the primary coupling reaction last in the reaction sequence thereby eliminating the potential interference from the primary binding reaction.

The second step of route 2 has some attendant parameters that primarily are directed to reaction efficiency. The reactants should have sufficient solubility in the reaction medium to enable relatively facile coupling to take place. Generally, this solubility will be preferably about 0.05 to 2M for the reactants and 1 to 100 $\mu$M for the enzyme. When the solubilities of the reactants of the coupling reaction are less than this, route 1 is preferentially employed.

Specific embodiments of labels, support materials and bioactive agents that can be coupled to proteins by synthetic route 2 are shown in Table 1.

TABLE 1

Amino Acids for Coupling Labels, Bioactive Agents
and Supports to Antibodies (Potential Applications are
listed along with the chemical names of the Amino Acids)

| | | |
|---|---|---|
| $HOCH_2CH(NH_2)CO_2H$ | $H_2NCH_2CH_2SO_3H$ | $I(OH)C_6H_3CH_2CH(NH_3)CO_2H$ |
| Serine | Taurine | Iodotyrosine |
| $^3H$, $^{14}C$ | $^3H$, $^{14}C$, $^{35}S$ | $^{129}I$, $^{131}I$ |
| Radioactive Label | Radioactive Label | Radioactive Label |
| | $H_2NCH_2CH_2PO_3H$ | $FC_6H_4CH_2CH(NH_2)CO_2H$ |
| | Aminoethanephosphonic Acid | Fluorophenylalanine |
| | $^3H$, $^{14}C$, $^{32}P$ | NMR Label |
| | Radioactive Label | |
| | $^{31}P$ - NMR Label | |

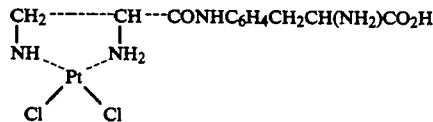

Metal Chelate
Platinum for Electron Microscopy
and X-ray Labels
Cobalt for Ratiation Therapy fluoroescenyl $NHCSNH(CH_2)_4CH(NH_2)CO_2H$
Lysylfluorenscene
Fluoroescent Label $(NO_2)_2C_6H_3NH(CH_2)_4CH(NH)CO_2H$
Bisnitrophenyllysine
Fluorescent Label
Antigenic Label

Biotin Group for Complex
Attachment to Avidin-Resin or as
Label for Enzymatic Detection $H_2C\!=\!HCH_2NH + CH_3CH\!=\!CHCH\!=\!CHCO_2\text{-(attached substance)}$
Diels-Alder
For Attachment of Resin
or other attached substance $H_2C\!=\!CHCONH(CH_2)_4CH(NH_2)CO_2H + H_2C\!=\!CHCONH\text{-(H or attached substance)}$
Free Radical Polymerization

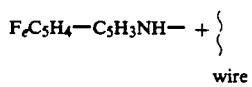

wire

Magnetic Process

Linker Arm

There are several reasons why the linker arm version of routes 1 and 2 would be selected according to the invention. First, the environment of the carboxyl terminus may prevent approach of a large, bulky auxiliary substance. Second, the auxiliary substance may not contain functional groups that are specifically reactive with the side chain of the nucleophile. Third, the linker arm increases the distance between the auxiliary substance and the protein which can help maintain the activity of the protein. Fourth, the protein can more freely adopt a spatial conformation that is appropriate for its reactivity. Fifth, it will lessen or minimize alteration of protein confirmation caused by carrier material proximity.

The structure of the linker arm includes functional groups at the ends of a flexible to semi-flexible chain. One of the functional groups is the specifically reactive group mentioned above that reacts with the side chain of the nucleophile. The other functional group of the linker arm is chosen to readily react with available combining groups on the auxiliary substance. Of course, this pair of groups of the linker arm is selected so that one does not substantially interfere with the other when they are used in the binding and combining reactions.

In both synthetic routes, the step to combine linker arm and attached substance is accomplished before the binding reaction with the nucleophile. Since protein and nucleophile are not present during this step, the kinds of reactions available are numerous. If the combining group of the auxiliary substance is an aldehyde group, the other functional group may be an amine (Schiff base product), an activated acid such as an iminocarboxy, carboxyalkoxy or acid halide (amide product) or epoxy (substituted amine product). If the combining group of the auxiliary substance is an hydroxy group, the other functional group may be an activated acid or ester (ester product) or activated alkyl such as a halo alkyl, alkyl tosyl or alkyl mesyl (ester product). If the combining group of the auxiliary substance is an acid group, the other functional group may be an amine (amide product) or activated hydroxyl (ester product). If the combining group of the auxiliary substance is a chelating agent, the other functional group may be a bound metal group. Other pairs of reactants include water soluble carbodiimide and amino; N-acyl succinimide and amino; and olefin and diene as well as those described above under part (3) of the primary binding reaction for route 2. Of course, the reverse order of reaction is also possible.

The backbone of the linker arm may be any that provides a flexible or semi-flexible chain. Included are polymers and oligomers of amides (peptides), olefins, esters, carbonates, urethanes, ethers, glycidyl, epoxides and the like. Also included are alkylene and hydrocarbon chains. The length of the backbone may be from about two to about 100 atoms or monomeric units, preferably about four to about 20 atoms or monomeric units in length. Examples of the backbone include hexylenyl, decylenyl, poly(4-aminobutyric acid), poly(glycyl), poly(glycylalanyl), poly(4-hydroxybutyric acid), polylactones, poly(bisphenol-A-diglycidyl ether) and polyacrylamide.

Proteins

The types of proteins (including peptides as small as two residues) that can be coupled according to the present invention are active proteins with polypeptide chains containing reactive carboxyl termini. Examples of suitable proteins include enzymes, enzyme inhibitors, hormones including peptide hormones, antibodies, $F_{ab}$ truncated antibodies, functional proteins, transcriptases, reading frame proteins, DNA binding proteins and other biologically active polypeptides.

With respect to labeling, monoclonal or polyclonal antibodies, antibody light and heavy chains, antibody fragments, epitopal sites of antibodies, chimeric antibodies, CDR antibodies, DNA binding proteins, enzymes, and reading frame proteins are preferred as proteins. As used herein, the term "antibody fragments" includes variable or constant regions of antibody chains, Fab or F(ab')2 and Fc fragments, light and heavy variable chains, epitopal regions of light or heavy antibody chains, combinations of such regions and chains, and recombinations of a particular fragment with a complementary fragment isolated from the same antibody or a different source of antibody, to form, for example, chimeric human-mouse antibodies carrying human constant regions, or altered human antibodies carrying hypervariable segments derived from antibodies from a differing mammalian source. The antibodies and antibody fragments are generally useful in the diagnosis of diseases, disorders, or hereditary dysfunctions. The antibodies are also generally useful in separation techniques and for detection of antigenic material. This includes mammalian immunoglobulin proteins from the IgA, IgD, IgE, IgM, or IgG class of immunoproteins.

With respect to immobilization, mono or polyclonal antibodies and enzymes are preferred as proteins.

With respect to bioactive agents, mono or polyclonal antibodies, peptide hormones, histocompatibility proteins, polypeptide inhibitors, peptide toxins, structural proteins (eg. collagen), globular proteins and fibrous proteins are preferred as proteins.

Nucleophile Chosen as an Amino Acid

A wide variety of amino acid nucleophiles can be used in the present invention. Generally these include alpha amino acids with neutral, basic or acidic side chains wherein the side chains may contain the reactive substituents mentioned above. The choice of amino acid for labeling antibodies, binding proteins to immobilizing support, or binding bioactive agents to proteins is generally coordinated with the enzyme and the protein chosen. Certain enzymes will couple specific amino acids to the carboxyl termini of proteins. For example, CPD-Y will generally couple amino acids with neutral or basic side chains to antibodies. Certain other enzymes, which utilize cysteine and/or serine at their enzymatic sites and are derived from plant and microbial sources, will couple amino acids with acidic side chains to proteins.

Furthermore, in order to perform the binding reaction, the amino acid nucleophile will exhibit a distinctive reaction character. This will allow its selective binding to the auxiliary substance or its combination with linker arm. The distinctive character results from the reactive substituent of the side chain of the nucleophile as explained above. This reactive substituent may be a sulfhydryl, hydroxy, activated hydroxyl, phosporamidoyl, hydrazinyl, amino, azidyl, epoxy, acid, boronyl, activated esters, ferrocentyl, ferro complex or olefinyl group, mixtures thereof and other functionally reactive groups.

Embodiments of these amino acid nucleophiles include aliphatic amino acids such as monoamino monocarboxylic acids, e.g., glycine, alanine, valine, norvaline, leucine, isoleucine, and norleucine (useful as radioactive label); hydroxy amino acids such as serine, threonine, and homoserine; sulfur-containing amino acids such as methionine, cystine, cysteine, and taurine (for linker arm or auxiliary substance binding); diamino monocarboxylic acids such as orthinine, lysine, and arginine (for linker arm or auxiliary substance binding); and monoamino dicarboxylic acids such as aspartic acid and glutamic acid (for linker arm or auxiliary substance binding). Also, aromatic amino acids, such as phenylalanine and tyrosine; heterocyclic amino acids, such as histidine and tryptophan, and olefinic amino acids such as 2-amino-2-vinyl acetic acid (for linker arm or auxiliary substance binding) are included within the group of amino acids of the present invention.

Additional amino acids are those with the C-terminal end protected. This includes, for example, amides, anilides, hydrazides, esters, and the like.

Preferred classes of amino acid nucleophile include aliphatic amino acids, hydroxy amino acids, their activated derivatives, phosphoramidoyl amino acids, sulfur-containing amino acids, diamino monocarboxylic acids, activated ester amino acids, aromatic amino acids and heterocyclic amino acids. Especially preferred embodiments include serine, alanine, phenylalanine, taurine, lysine, arginine, 2-aminopenta-4-enoic acid and cysteine. Also included are carboxyl protected amino acids, such as amides and esters.

Nucleophile Chosen as an Amine

The amine nucleophile includes any $C_2$ to $C_{20}$ primary amine that has another reactive substituent along its backbone as described above. Alternatively, it may have a simple, nonfunctional side chain in circumstances where it is also the auxiliary substance. In addition to being a decarboxy analog of the amino acid nucleophile, the amine nucleophile may also have a side chain substituted by hydroxyl, sulfhydryl, activated hydroxyl, epoxy, amino, azidyl, olefinyl, activated ester, hydrazinyl, phosphoramidoyl, boronyl, iminyl, amidinyl, ferrocentyl, ferro complexes or other functionally reactive groups. Alternatively, it may have a simple, nonfunctional side chain in circumstances where it is also the auxiliary substance.

Nucleophile Chosen as an Alcohol

The alcohol nucleophile includes any $C_1$ to $C_{20}$ primary alcohol that has another reactive substituent along its backbone. The reactive substituent may be a hydroxyl, sulfhydryl, activated hydroxyl, epoxy, amino, azidyl, hydrazinyl, olefinyl, activated ester, phosphoramidoyl, boronyl, iminyl, amidinyl, ferrocentyl, ferro complex groups, mixtures thereof or other functionally reactive groups. Alternatively, it may have a simple, nonfunctional side chain in circumstances where it is also the auxiliary substance.

Labels

Labels for the proteins according to the present invention include labeled, or tagged amino acids having a variety of substituents or atoms that possess properties suitable for detection by conventional techniques. Such properties include photoaffinity, magnetism, radioactivity, fluorescence, enzymatic activity, electron dense (x-ray), nuclear magnetic resonance, electron spin resonance, antigenicity, and phosphorescence. For example, amino acids can be labeled with either $^{14}C$ or $^3H$ atoms. Further, the amino acids may be tagged by known fluorescent dyes, porphyrins, colorimetric dyes, reactive groups and antigens or enzymatic substrates that permit spectroscopic, photographic or radiometric detection. See E.T. Koh, et al., *Biotechniques*, 7, 596 et seq. (1989); S. Borman, "Bioconjugate Chemistry Attracts Growing Interest" in the May 8, 1989 issue of "Chemical and Engineering News" at p. 25 et seq., the disclosures of which are incorporated herein by reference.

Enzymes

Enzymes capable of coupling the nucleophile to the protein are exopeptidases, i.e., enzymes capable of acting specifically at the carboxyl terminal end of peptide chains. See J.S. Fruton In "Advances in Enzymology", in the chapter entitled Reagents for Protein Modification as cited above. They form or transform peptide bonds and are relatively stable under the reaction conditions used.

Carboxypeptidase enzymes are generally known to cleave the C-terminal peptide bond in polypeptides. They exhibit alternative enzymatic activities that are pH-dependent. For example, transpeptidation, transesterification and condensation products can be formed by the pH dependent action of carboxypeptidase Y.

Preferred carboxypeptidases according to the invention include serine and cysteine (eg. hydroxy and thiol) carboxypeptidases. Certain of the serine and cysteine enzymes are capable of attaching amino acids and aliphatic amines with neutral or basic side chains to the carboxy termini of proteins. Examples of these enzymes include carboxypeptidase Y (CPD-Y), penicillocarboxypeptidase S-1 and S-2, carboxypeptidase C and $C_N$, malt carboxypeptidase I and II, phaseolin; and carboxypeptidase A, carboxypeptidase B and metalloproteases, which perform the condensation reaction only. Certain other of the serine carboxy peptidase enzymes are capable of attaching amino acids and aliphatic amines having acidic side chains to the carboxy termini of proteins.

Carboxypeptidase Y is a preferred enzyme for use in this invention. CPD-Y is an enzyme from yeast fungi possessing a serine residue in its catalytic site, and is characterized by its ability to catalyze various reactions depending on the pH of the reaction mixture. Furthermore, CPD-Y is a preferred enzyme for use in the labeling process of the present invention because it rapidly transpeptidates.

It is to be understood that the enzyme may be immobilized or chemically modified to retain or improve stability and appropriate enzymatic activity. It is also to be understood that the enzyme source may be yeast, animal, vegetable, or microbial. Enzymes produced by the technique of molecular cloning, either of naturally occurring enzymes or synthetically produced by mutation or recombination, are also included in the invention.

Immobilizing Supports

Immobilizing supports useful in the present invention are inorganic or organic materials functionalized so that a reaction can occur between the nucleophile or linker arm and the support. When the former reaction is employed, the support will be functionalized with a specifically reactive group mentioned above. When the latter reaction is employed, the support will be functionalized with the combining group for the other functional group mentioned above. In this case also, the reactive substituent may be chelating ferromagnetic groups. The immobilizing support then has the appropriate character to produce binding. With a ferromagnetic group, the support may be magnetic wire that is rendered inert to the reaction medium eg. with teflon. Passing a current through the wire will establish the magnetism needed to cause binding. Alternatively, a magnet external to the system (i.e. outside the chromatographic medium) can be used to cause binding to the support. With the chelating group, the support may be an immobilized metal or other chelate.

The support may be a porous or semiporous solid. Preferably, it is biologically inert and insoluble. Materials that may be used as supports include fibers, sheets, microspheres, particles, microparticles, beads, microbeads, platelets, membranes, and the like.

The surface of the immobilizing support of the present invention is preferably porous. The use of substances having a porous surface, such as substantially spherical polymeric beads or microspheres of agarose allows large surface areas for the attachment of protein at high density. A surface is considered porous where the size of the majority of the pores in the material is sufficiently large so as to allow the migration of the protein into the interior of the spheres. The size and shape of the support may be varied widely, depending on the particular protein and its intended use.

The immobilizing supports include a wide variety of substances. The choice of support, however, depends upon the choice of the nucleophilic and/or linker arm as well as on the intended use of the immobilized protein. The coupling reactions, nucleophile, specifically reactive group and reactive group all are compatible as described above. In particular, the support is chosen such that the nucleophile will readily couple to the support or support-linker arm combination in preference to any other reactive sites on the protein. For example, cysteine may be used as the amino acid nucleophile to couple with a protein with no sulfhydryl groups eg. an antibody. A support or support-linker arm specifically reactive group is chosen that would react with the sulfhydryl moiety, for example, an organometallic group such as an organo mercury compound. Alternatively, 2-amino-hex-4-enoic acid may be the amino acid nucleophile, and a specifically reactive group for the support may be one that would specifically react with the unsaturated side chain, as for example through a Diels Alder reaction. Another alternative is the choice of a photoaffinity label such as N-hydroxy succinimidyl-4-azidosalicylic acid side chain, and an arylamine as the specifically reactive group on the attached substance. This salicylic side chain is to be coupled to the epsilon amino group of a lysine before the photo addition so that it will not be reactive with the amino groups of the protein. Photoreaction under, for example, u.v. light, will accomplish the desired photo binding reaction. Moreover, if a linker arm is used, available groups on the support act as the reactive group. The other functional group of the linker arm is appropriately chosen to bind with the reactive group.

Bioactive Agents

Included within the invention is a method for attachment of a bioactive agent to a protein at a site remote from the active site. These bioactive agents can be carried or transported by the protein to a site where they can perform a desired reaction.

The bioactive (biologically active) agent includes physiologically or pharmacologically active substances that act locally or systemically in the body. Examples of biologically active agents include peptide drugs, protein drugs, desensitizing agents, antigens, vaccines, anti-infectives, antibiotics, antimicrobials, antiallergenics, steroidal anti-inflammatory agents, decongestants, miotics, anticholinergics, sympathomimetics, sedatives, hypnotics, psychic energizers, tranquilizers, androgenic steroids, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, $\beta$-adrenergic blocking agents, nutritional agents, metal compounds, anti-cancer compounds such as fluorinated nucleotides, nucleotide analogs, cytosine arabinocide, 5-fluorouracil, ricin-A, tetanus toxin, cyclic therapeutic peptides such as anamycin, erythromycin, cyclosporin, AZT, and alkaloids. Also, various forms of the biologically active agents may be used. Forms such as uncharged molecules, molecular complexes, salts, ethers, esters, and amides are included.

The bioactive agents are functionalized to carry specifically reactive groups for coupling to the nucleophile directly. Alternatively, appropriate available combining groups on the bioactive agent can be reacted with the other functional group on a linker arm. Preferably, this functionalization will be accomplished with a group already present within the agent.

Conditions for Primary Coupling Reaction

The conditions for the primary coupling reaction efficiently favor condensation, transpeptidation or transesterification over peptide cleavage. As can be seen from the following discussion of the application of the primary coupling reaction to antibody protein, these conditions generally involve control of pH, temperature, reactant concentrations, enzyme concentration and incubation time.

The conditions for condensation and transpeptidation are basic which also disfavors peptide cleavage by hydrolysis. They are within a pH range in which the amine group of the nucleophile is not protonated, i.e., it is in the free base form. Typically, this range is about pH 8.5 to 11. The selection of condensation over transpeptidation is made kinetically in that transpeptidation is completed quickly while condensation occurs slowly. In particular, transpeptidation occurs between 5 seconds and 1.4 hours while condensation occurs between 2 and 24 hours.

Transesterification occurs under moderately acidic conditions which disfavor hydrolysis. Preferably the pH is less than about 6 and greater than about 3. A high molar concentration of the alcohol nucleophile is also important for transesterification.

The reaction temperature is the functional range of the enzyme, preferably up to about 40° C.

The concentrations of the reactants and enzyme are adjusted to provide optimum results. Generally, the highest possible concentrations of enzyme nucleophile and protein are used that coincide with an appreciable primary coupling reaction rate. Preferably, the protein is present at a concentration of from about 1 $\mu$M to about 1M, especially up to about 1 mM when the protein is an antibody. The nucleophile or intermediate incorporating the nucleophile is preferably present at a concentration of at least 0.05 molar and especially a concentration of from about 0.1 to 2 molar. The enzyme is preferably present at a concentration of about 1 pM to 1 mM.

The incubation time (reaction time) of the protein and the nucleophile is from about 0.2 to 10 hours, preferably from 1.0 to 8 hours for condensation while for transpeptidation or transesterification, it is from about 30 seconds to about 1.5 hours.

Specific Embodiments, Antibody Protein

The pH of the reaction between an antibody and nucleophile determines the dominant enzymatic activity exhibited by the carboxypeptidase enzymes. Different reaction courses are possible at different pH values. The incorporation of a nucleophile by condensation, transpeptidation or transesterification depends upon which reaction course dominates in the incubation mixture.

At neutral pH values, hydrolysis of peptide bonds (peptidase activity) is generally considered to be the dominant activity. As the pH increases, the hydrolysis activity decreases and the condensation and transpeptidation reactions become the prominent activities of the enzyme. When the pH is maintained at a level that provides the free base form of the nucleophile, typically from about 8.5 to 11.0, preferably 9.5, the transpeptidation and condensation reaction are favored with the former being kinetically favored (i.e. happens fast). Typically, the transpeptidation reaction is preferred over condensation because it occurs rapidly in about 30 seconds to about 1 hour. When the pH is low such as 3.0 to 6.0 and the molar concentration of alcohol nucleophile is high, transesterification is favored. This reaction cleaves the C-terminal amino acid residue of the protein and substitutes the alcohol nucleophile by enzyme displacement.

Figure 1B:
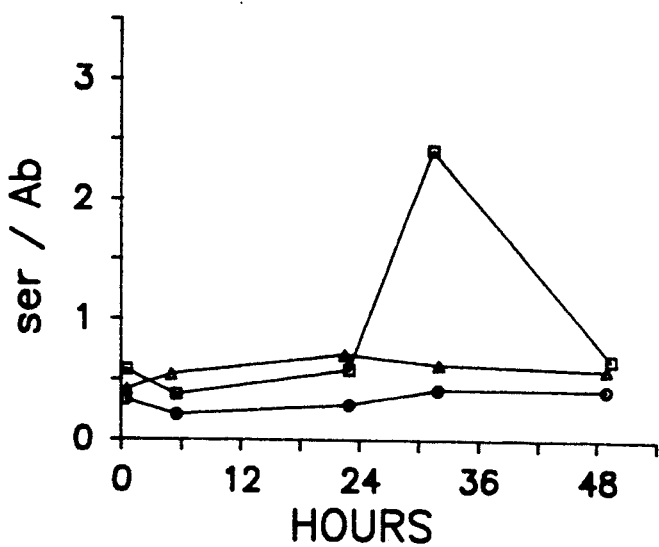
FIG. 1B is a graph of the pH dependence of the incorporation of serine in an antibody with respect to time at 25° C.
Figure 1C:
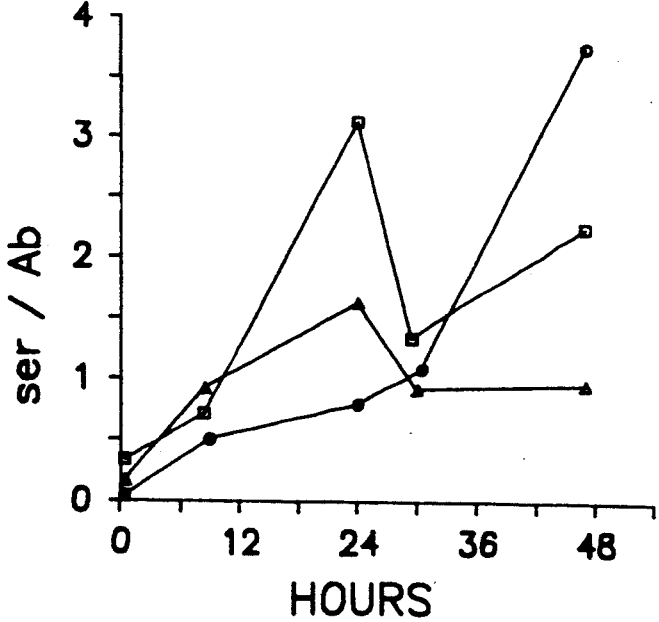
FIG. 1C is a graph of the pH dependence of the incorporation of serine in an antibody with respect to time at 37° C.

In several studies, the pH dependence of amino acid nucleophile addition by condensation with an antibody was examined and the details are described in the following examples section. The results of these studies, as depicted in FIG. 1, show that nucleophile incorporation is higher at higher temperatures and at higher values of pH. At a pH of 7.5, the nucleophile incorporation was observed to increase initially, followed by a decrease in incorporation and then an additional increase. The first incorporation is due to transpeptidation. The decrease in incorporation is due to partial loss of the incorporated nucleophile by the disfavored hydrolysis reaction. The second incorporation is due to the slower addition of the nucleophile by condensation.

The effect caused by variation of the concentration of the reactants in the incubation mixture was also studied and the results are shown in Table 2. As generally indicated above, concentration directly affects rate and amount of incorporation. The details of the study are provided in the following examples section.

TABLE 2

Effect on Condensation Reaction of Variation of Incubation Conditions

| Time$^a$ (hrs) | Ab$^b$ (mg/ml) | Ser$^b$ (mM) | CPD-Y$^c$ (μM) | SER/Ab$^d$ Ratio | Comments$^e$ |
|---|---|---|---|---|---|
| 8 | 4.1 | 230 | 20 | 3.3 | Antibody Conc. |
|  | 12.7 | 234 | 20 | 4.7 | Varied |
|  | 18.8 | 232 | 20 | 1.2 |  |
| 9 | 12.3 | 0 | 20 | 0.16 | Serine Conc. |
|  | 12.3 | 110 | 20 | 0.14 | Varied |
|  | 12.3 | 220 | 20 | 1.34 |  |
|  | 12.3 | 330 | 20 | 1.68 |  |
| 11.5 | 10.5 | 122 | 5 | 0.14 | CPD-Y Conc. |
|  | 10.8 | 112 | 11 | 0.15 | Varied |
|  | 11.8 | 120 | 16 | 1.6 |  |
| 8 | 7.7 | 111 | 20 | 2.4 | No Cosolvent |
|  | 7.7 | 175 | 20 | 4.2 | 30% glycerol |
| 27 | 10.5 | 78 | 20 | 0.4 | F1-monoclonal |
|  | 11.1 | 78 | 20 | 16.9 | F1-polyclonal |

$^a$Time of labeling incubation at 37 C., pH 9.5.
$^b$Measured concentration in incubation mixture (Ab = antibody).
$^c$Calculated from concentration of stock solution.
$^d$Molar ratio, determined as described in methods section. The data shows results of a single representative experiment. Each experiment was repeated several times with similar results.
$^e$Measurement made or change from standard method (see text for details).

The distribution of the nucleophile (labeled amino) acid between the carboxy termini of heavy and light chains of the antibody was also investigates, and the details are given in Example 4. The results indicate that the labeled amino acid is preferentially incorporated into the heavy chain. At least about 70 percent of the incorporated nucleophile is located on the heavy chain. Generally, the L-isomers of amino acids are incorporated by this method, with incorporation occurring substantially completely at the carboxyl termini of the heavy chains of antibodies.

Although the light chain of the antibody is labeled by this reaction to a certain extent, it is not located near the antigen-binding region. Therefore, little effect, if any, on the function of the antibody is noted as a result of this interaction.

The antigen-binding capacity of the labeled antibodies as compared to that of the unlabeled antibodies was also studied. (See Examples 5 and 6.) For the anti-asparagine synthetase antibodies the average binding capacity was determined to be 100.1 percent of the binding capacity with 0.6 serines incorporated per antibody. The anti-F1 antibodies labeled as in Table 2 were also assayed to determine their binding capacity. The binding capacity was found to be 105 percent for the monoclonal antibody and 114 percent for the polyclonal antibody compared to the unlabeled controls. These values are an average of four determinations. The slight increases found for the labeled antibodies over the controls are due to experimental errors and are not significant. These results show no significant loss of antigen binding as a result of label attachment.

Similar reaction conditions of temperature, pH, and concentrations can be established for protein incorporation of any of the amino acid or amine nucleophiles or intermediates as mentioned above.

Demonstration of Attachment

The results of some experiments wherein other amino acids were used as radioactive labels are shown in Table 3. The condensation reactions were carried out generally as described in Example 9 and assayed for label incorporation as described in Example 3. The concentrations of antibody and amino acid shown in Table 3 represent actual measured concentrations. The concentration of carboxypeptidase Y is calculated from the concentration of the stock solution used. The values of label incorporation are given as label incorporated per antibody molecule above the value of the control, which was incubated under the same conditions without the addition of enzyme.

TABLE 3

| | Condensation to Attach Nucleophile | | | | |
|---|---|---|---|---|---|
| Time$^a$ (hrs) | Ab$^b$ (mg/ml) | Label$^b$ (mM) | CPD-Y$^c$ (μM) | Label/Ab$^d$ Ratio | Label$^e$ Type |
| 8.5 | 8.7 | 188 | 20 | 0.5 | Taurine |
| 8.5 | 14.6 | 44 | 20 | 1.2 | Alanine |
| 8.5 | 18.8 | 232 | 20 | 1.2 | Serine |

$^a$Time of labeling incubation at 37° C., pH 9.5.
$^b$Measured concentration in incubation mixture (Ab = antibody).
$^c$Calculated from concentration of stock solution.
$^d$Molar ratio.
$^e$Amino acid used for labeling reaction.

Although some quantitative variation in the amount of label incorporation was observed in duplicate experiments conditions, this was within experimental error. The variation was probably due to the difficulty of the separation required for the accurate assessment of the label incorporation. High concentrations of unbound label were essentially completely and rapidly separated from the relatively small quantities of antibody. Some small amount of label, however, apparently remained at times, causing quantitative fluctuations in measured label incorporation. For this reason, it was necessary to include a control sample lacking carboxypeptidase Y for each determination. As an added precaution, the trailing portion of the antibody peak was not included in the quantitation.

As shown in Table 3, the enzyme incorporates alanine to about the same degree as serine. The enzyme was also found to incorporate taurine, an amino acid not usually found in proteins. The incorporation of taurine was found to be somewhat limited by the solubility of the free amino acid, however.

This method of binding an antibody to a nucleophile provides a means of immobilizing, labeling or augmenting antibodies without loss of antigen-binding capacity. This is due to the primary coupling reaction of the nucleophile with the antibody by condensation, transpeptidation or transesterification.

Various nucleophiles can be bound to other functional proteins using similar experimental parameters.

The amino acid or amine nucleophile, enzyme, protein, and bioactive agent, label or immobilizing support, however, are generally chosen so as to enhance specific binding and reduce nonspecific binding. In this way, the bioactive agent, label or immobilizing support can be bound to a protein remote from its functional site.

The invention will be further characterized by the following examples. These examples are not meant to limit the scope of the invention that has been set forth in the foregoing description. Variation within the concepts of the invention are apparent to those skilled in the art.

Examples 1-8 are standard methods for condensation, transpeptidation and transesterification. Example 9 demonstrates condensation. Examples 10 and 11 demonstrate transpeptidation. Examples 12 and 13 demonstrate transesterification.

EXAMPLE 1

Antibody Preparation

Anti-asparagine synthetase monoclonal antibodies and anti-F1 ATPase monoclonal and polyclonal antibodies were obtained from laboratory stocks. Monoclonal antibody stocks were obtained in the form of mouse Ascites tumor fluids and polyclonal antibody stocks were obtained from rabbit serum. Antibodies from either source were purified by addition of solid ammonium sulfate to a concentration of 50% of the saturation level. The precipitated protein was collected by centrifugation and dissolved in a minimal amount of 10 mM Tris-HCl [Tris, tris(hydroxymethyl)aminomethane](pH 7.5). The preparation was then subjected to a second ammonium sulfate treatment until a 50% saturation level was reached. The precipitate was then collected by centrifugation. The purified antibodies were dissolved in a minimal amount of water and dialyzed for 18 to 24 hours against 10 mM sodium bicarbonate at 4° C. This dialysis step was necessary to remove the residual ammonium sulfate that was found to inhibit the activity of carboxypeptidase Y. The purified antibodies were stored in aliquots at −20° C. until needed.

Unless otherwise noted, these three antibodies were used in each of the following examples. The term "antibody" as used herein means anti-asparaginine synthetase monoclonal antibody, and anti-F1 ATPase mono and polyclonal antibodies.

EXAMPLE 2

LABEL PREPARATION

Serine was used initially as $^3$H-serine and in latter experiments $^{14}$C-serine was used. All other amino acids used were $^3$H-amino acids. Radioactive amino acids were purchased from Amersham (Arlington Heights, IL). Unlabeled serine was from Fluka (Ronkonoma, NY). Radioactive amino acids were diluted with unlabeled amino acid to, a specific activity of 0.5 to 2 mCi per millimole. The diluted amino acid was then purified by repeated precipitation with ethanol at −20° C. These precipitation steps were required to reduce nonspecific binding of the amino acid to the antibodies. The amino acid was stored as an aqueous solution at 4° C.

The specific activity of the diluted, purified amino acid was determined as follows, and used in subsequent calculations of label incorporation. The quenched, detectible radioactivity was determined under conditions identical to those used in the measurement of label incorporation. A known volume of the amino acid solution was diluted to 1.0 ml with 0.1 M sodium phosphate (pH 6.8). This diluted sample was counted in a Beckman LS-100 liquid scintillation counter (Beckman Instruments, Fullerton, CA) with 10.0 ml 3a70b scintillation fluid (Research Products, Elkgrove, IL). The amino acid concentration of the stock amino acid solution was determined on a known volume by assay of the amino groups with the ninhydrin assay; see S. Moore et al., *J. Biol. Chem.*, 157, 367 (1948). A standard solution was prepared for this assay by dissolving glycine in water at 0° C. to obtain a saturated solution. The liquid was separated from any undissolved solid glycine, warmed to room temperature, and used as a standard. The concentration of the standard was assumed to be 1.89 M; see J. B. Dalton et al., *J. Biol. Chem.*, 103, 549 (1933). From these measurements, the quenched value of CPM/mmole was calculated and used in subsequent calculations.

EXAMPLE 3

LABEL INCORPORATION ASSAYS

The unbound amino acids were separated from the antibody by gel filtration HPLC. A 20 μl sample of the reaction mixture after incubation was applied to a GPC-300 gel filtration column (Synchrom, Linden, In) and eluted with 0.1 M sodium phosphate (pH 6.8). The HPLC system employed for this purpose consisted of a dual pump gradient system and a variable wavelength UV monitor produced by ChemResearch (ISCO, Lincoln, NE). The absorbance peak, monitored at 280 nm, corresponding to the antibody was collected. In order to ensure that complete removal of the unbound amino acid from the antibody, only the first ⅔ of the absorbance peak was collected. The collected antibody solution was diluted to 1 ml with the elution buffer.

Figure 2:
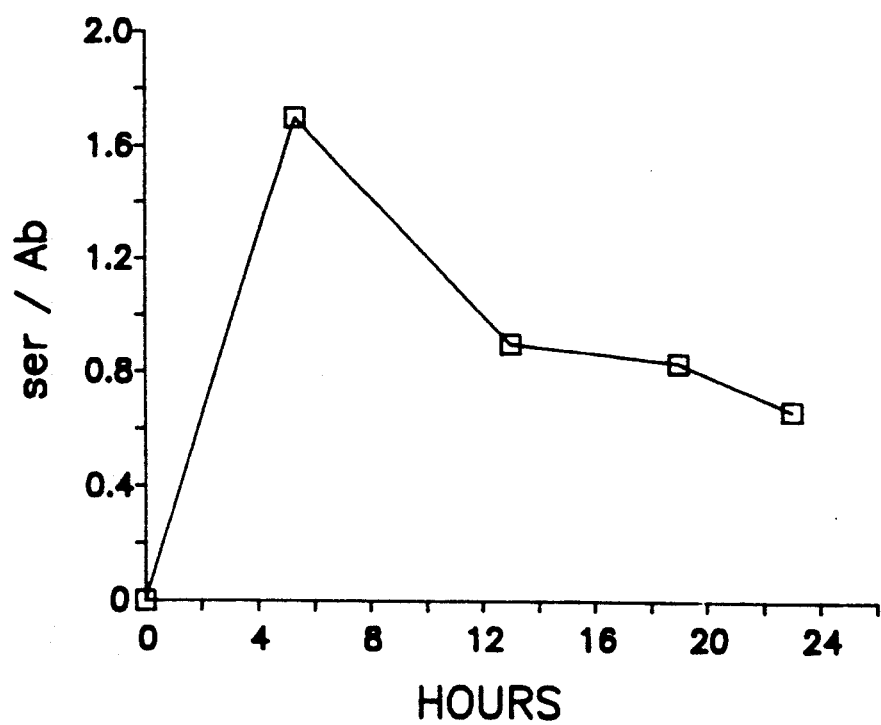
FIG. 2 is a graphical representation of the effect of incubation time on serine incorporation.

The antibody concentration in the collected solution was determined by measurement of the absorbance at 280 nm, assuming a standard absorbance of 1.46 absorbance units/mg. The incorporated amino acid was determined by counting 1.0 ml of the collected antibody solution using 10 ml 3a70b liquid scintillation fluid. The amount of label incorporated was calculated using the corrected specific activity for the amino acid described above. The molar concentration of the antibody was calculated assuming a molecular weight of 150,000; see I. Roitt et al., *Immunology*, C. V. Mosby Co., St. Louis, p. 5.3 (1985). The reported label incorporation is the difference between the values obtained for the samples with and without carboxypeptidase Y. The results of the label incorporation are discussed in the foregoing specific embodiments section in conjunction with FIG. 2.

EXAMPLE 4

ANTIBODY CHAIN SEPARATION

This example shows the specificity of nucleophile coupling to the heavy chain of an antibody as discussed in the foregoing specific embodiments section.

Separation of the heavy and light chains of the antibody was performed on both labeled and control (unlabeled) antibodies. The samples were labeled as described above. Following the incubation, the antibodies were precipitated by addition of ammonium sulfate to a concentration of 50% of saturation. The precipitate was collected by centrifugation and the pellet was dissolved in a denaturing buffer (pH 6.8) consisting of 100 mM sodium sulfate, 2 M urea, 2% sodium lauryl sulfate (SDS), 1% B-mercaptoethanol, and 25 mM 4-morpholine ethanesulfonic acid (MES). The sample was incubated at 100° C. for 5 minutes to ensure complete denaturation of the protein. The antibody chains were separated by gel filtration HPLC using an Altex TSK-125 column (Biorad, Richmond, CA) equilibrated with the denaturing buffer. The effluent was monitored at 280 nm. The peaks corresponding to the heavy and light chains of the antibody were collected separately. The collected samples were diluted to 1.2 ml with the denaturing buffer.

The amount of amino acid incorporated into each chain was determined by counting 1.0 ml of each sample with 10 ml 3a70b liquid scintillation fluid. Due to interference of the denaturing buffer components the amount of protein in each sample could not be determined by the methods used above or by other commonly employed methods. An assay developed for this purpose consisted of adding 25 $\mu$l of 30% acrylamide, 0.8% bioacrylamide, to 50 $\mu$l of the sample to be assayed. The mixture was polymerized by addition of 1.5 $\mu$l 1 10% ammonium persulfate and 1 $\mu$l N,N,N',N' tetramethylethylenediamine. The interfering buffer components were separated from the solidified sample by washing with 2 aliquots (2ml) 10% trichloroacetic acid, 3 aliquots (2ml) 10% acetic acid and 3 aliquots (2ml) 5% methanol, 7.5% acetic acid. The protein was stained with Coomassie Blue R-250 (Commission on Biological Stains Number 42660). Following extensive washing with 30% methanol, 7.5% acetic acid to remove unbound dye, the bound dye was eluted by incubation with SDS, sodium bicarbonate, and methanol. The absorbance of the eluted dye was measured and the protein content of the sample was determined by comparison with standard protein solutions assayed in an identical manner.

The measured protein content and amino acid incorporation for each chain were used to calculate the label incorporation per polypeptide chain. In these calculations, the molecular weights of the heavy and light chains were taken to be 50,000 and 25,000, respectively; see I. Roitt et al., vide supra. The results based upon the data obtained (not shown) are discussed in the foregoing specific embodiments section and indicate at least a 70% incorporation in the heavy chain.

EXAMPLE 5

ANTI-ASPARAGINE SYNTHETASE ANTIBODY IMMUNOPRECIPITATION

This example shows that the attachment of the nucleophile does not affect the antigen binding capacity of the antibody as discussed in the foregoing specific embodiments section.

Antibodies, both labeled as described above and controls, were assayed by immunoprecipitation to determine their capacity to bind antigen. An aliquot of the incubation mixture was assayed to determine the extent of label incorporation. The remainder of the incubation mixture (80 $\mu$l ) was added to 420 $\mu$l of a pancreas extract containing asparagine synthetase; see C. A. Luehr et al., J. Biochem. Biophys. Methods, 3, 151 (1980). The pH of the mixture was adjusted to 7.5. Crude protein A extract (Sigma Chemical Co., St. Louis, MO) was washed twice by centrifuging the solution and suspending the pellet in 50 mM Tris-HCl (pH 7.5). This washed extract was suspended in 5 times its original volume of 50 mM Tris-HCl (pH 7.5). After incubation of the antibody with the pancreas extract for 18 hours at 37° C., 1 ml of crude, washed protein A extract was added and incubation was continued for an additional 2 hours. The mixture was then centrifuged to collect the Protein A/antibody/Asparagine Synthetase complex. The pellet was washed twice with 50 mM Tris-HCl (pH 7.5) and then incubated for 2 hours with 200 $\mu$l of an assay solution (pH 7.5) containing 100 mM Tris-HCl, 10 mM MgCl$_2$, 10 mM ATP, and 10 mM glutamine. The solid material was removed by centrifugation and the resulting solution was stored at $-20$° C. for amino acid analysis.

Amino acid analysis was accomplished by HPLC separation of the amino acids following derivitization with B-mercaptoethanol and o-phthaldialdehyde; see S. Unnithan et al., Anal. Biochem., 136, 195 (1984). The HPLC system used consisted of a dual pump gradient Beckman HPLC system with a Dupont model 836 fluorescence detector (E.I.Dupont, Des Plains, IL) and Integrator (Spectra-Physics, Santa Clara, CA). The column used was a Rainin Microsorb Cl reversed phase column (Rainin Instruments, Woburn, MA). The binding capacity of the antibodies was assessed by measurement of the hydrolysis of glutamine to glutamate by the asparagine synthetase bound to the Protein A/antibody complex. The activity of the bound enzyme was determined by the ratio of the integrated areas of the glutamate and glutamine peaks. The percent activity for the labeled antibodies relative to the unlabeled controls was calculated from these Glu/Gln ratios. The results generally indicate that the capacity of antibody with coupled nucleophile is the same as free antibody. See the discussion at pages 30 and 31.

EXAMPLE 6

ANTI-F1 ATPASE ANTIBODY IMMUNOPRECIPITATION

This example shows the same effect illustrated in Example 6.

Both monoclonal and polyclonal antibodies, labeled as described above and unlabeled controls, were assayed by immunoprecipitation to determine their capacity to bind antigen. An aliquot of the incubation mixture was assayed to determine the extent of label incorporation. The remainder of the incubation mixture (80 $\mu$l ) was added 420 $\mu$l of a 0.2 mg/ml solution of purified bovine F1-ATPase; see A. F. Knowles et al., J. Biol. Chem., 247, 6617 (1972). The pH of the reaction mixture was adjusted to 7.5. Crude protein A extract was washed twice by centrifuging the solution and suspending the pellet in 50 mM Tris-HCl (pH 7.5). This washed extract was suspended in 5 times its original volume of 50 mM Tris-HCl (pH 7.5). After incubation of the antibody with the pancreas extract for 18 hours at 37° C., 1 ml of crude, washed protein A extract was added and incubation was continued for an additional 2 hours. The mixture was then centrifuged to collect the Protein A/antibody/F1-ATPase complex. The pellet was washed twice with 50 mM Tris-HCl (pH 7.5) and then incubated for 2 hours with 100 $\mu$l of an assay solution (pH 8.0) consisting of 50 mM N-[tris(hydroxymethyl)-methyl]glycine (Tricine), 5 mM MgCl$_2$, and 5 mM ATP. The solid material was removed by centrifugation and the resulting solution was stored at $-20$° C. for analysis. An additional control lacking antibodies was treated similarly.

ATPase activity was determined by measurement of the released phosphate; see S. Unnithan et al., vide supra. The bound enzyme was assessed by the production of inorganic phosphate above the value given by the control which lacked antibody. The percentage of binding capacity of the labeled versus unlabeled antibodies was calculated as the ratio of the labeled to the unlabeled activities. The results are discussed in the specific embodiments section at pages 30 and 31.

EXAMPLE 7

STABILITY OF LABELED ANTIBODIES

The stability of the incorporated label under different storage conditions was also determined. For this experiment, label incorporation was assayed on an aliquot of the incubation mixture. The antibodies in the remainder of the sample were precipitated with ammonium sulfate and dissolved in water. An aliquot was stored at 4° C. and another at −20° C. for 8 days. Following the storage period the incorporated label in these samples was determined and compared to the first sample. The results are shown in Table 4.

TABLE 4

| | Label Stability | |
|---|---|---|
| Conditions[a] | Ser/Ab[b] | % of t = 0[c] |
| t = 0 | 0.55 | 100 |
| 8 days, 4° C. | 0.63 | 116 |
| 8 days, −20° C. | 0.49 | 88 |

[a]Storage conditions following labeling incubation at 37° C. and pH 9.5.
[b]Molar ratio, determined as described in methods section, average of two determinations.
[c]Average percent gain or loss of activity compared to no incubation following labeling incubation.

EXAMPLE 8

SPECIFICITY OF INCORPORATION

In order to verify that the incorporation is due to catalysis by the enzyme, L-serine at different concentrations and D,L-serine were incorporated by the standard method. These results are shown in Table 5. The incorporation of D,L-serine is comparable to incorporation of L-serine at half the concentration of the D,L-serine. If can be explained by the incorporation of only the L-isomer. This stereospecificity has been shown for carboxypeptidase Y under other conditions; see R. Hyashi et al., J. Biochem. 77, 69 (1975). Nonspecific absorption or other nonenzymatic means of attachment which might occur under these conditions would be expected to incorporate both isomers.

TABLE 5

| | | | Stereospecificity | | |
|---|---|---|---|---|---|
| Time[a] (hrs) | Ab[b] (mg/ml) | Ser[b] (mM) | CPD-Y[c] (lM) | SER/Ab[d] Ratio | Comments |
| 8 | 7.9 | 198 | 20 | 1.7 | L-serine |
| | 10.1 | 126 | 20 | 0.9 | L-serine |
| | 8.1 | 177 | 20 | 0.5 | D,L-serine |

[a]Time of labeling incubation at 37 C. pH 9.5.
[b]Measured concentration in incubation mixture.
[c]Calculated from concentration of stock solution.
[d]Molar ratio, determined as described in methods section.
[e]Label used.

EXAMPLE 9

STANDARD CONDITIONS FOR ANTIBODY LABELING (CONDENSATION)

The following conditions and methods for label incorporation by condensation were used for all runs unless otherwise indicated. A mixture of the antibody and amino acid stock solutions was made and diluted with water to the desired concentrations. The pH of this solution was measured with pH indicator paper (Fisher Chemical, Springfield, NJ) and adjusted to 9.5 with 0.5 M sodium From this solution a 4 μl portion was removed and diluted to 1.0 ml with 0.1 M sodium phosphate (pH 6.8). The absorbance of this solution was measured at 280 nm using a Beckman DU-50 spectrophotometer. The concentration of the antibody in the solution was calculated assuming a standard absorbance of 1.46 absorbance units per mg of antibody; see A. Good et al., in Selected Methods in Cellular Immunology, Mishell & Shiigi eds., W. H. Freeman & Co., San Francisco, p. 284 (1980). The concentration of the amino acid in the incubation mixture was determined by counting a small sample of the diluted mixture following further dilution to 1.0 ml with 0.1 M sodium phosphate (pH 6.8). The amino acid concentration was calculated from the counts present using the corrected specific activity determined previously and correcting for both dilutions, as well as the 5% dilution described below.

The remainder of the undiluted mixture was divided into two equal parts. To one of these portions was added the carboxypeptidase Y (affinity purified, E.C. 3.4.16.4, free from endoproteinase contamination) stock solution (24.3 mg.m/1) at 5 μl per 100 μl of mixture. The other portion served as a control and was diluted similarly with water. Once these two solutions were prepared, they were incubated in a 37° C. water bath for approximately 8 hours. The samples were then removed from the water bath and either analyzed immediately or frozen and used as soon as possible. The results of the variation in concentration of the label are provided in foregoing Table 2 and discussed in conjunction therewith.

EXAMPLE 10

TRANSPEPTIDATION WITH A TETRAPEPTIDE MODEL

This example illustrates the synthesis of the tetrapeptide Benzoyl-Thr-Val-Ser-(14 C)Ser from Benxoyl-Thr-Val-Ser-Ser. About 5 to 10 mM of Benzoyl-Thr-Val-Ser-Ser (BTVSS) may be dissolved in 2 ml of 50 mM sodium carbonate buffer (pH 9.5) containing 1 mM EDTA and 0.25 M 14-C-serine. The reaction may be initiated by the addition of 5 μM carboxypeptidase Y enzyme. At preset time intervals, the reaction may be sampled by removing 0.2 ml aliquots and diluting with 0.2 ml of acetonitrile, then adding 0.1 ml of 0.12 M acetic acid.

The samples may then be subjected to high pressure liquid chromatography (HPLC) using a reverse phase C-18 column developed with a linear gradient constructed from two solvents. A first solvent (A) can be 95% of 10 mM sodium acetate, 5% acetonitrile pH 4.5 and the second (B) can be 60% acetonitrile. A gradient can be developed over a 30 min time period and can be initiated by mixing solvents A and B at the proportions of 1 part A and 0 parts B and ended with 40 parts A and 60 parts B. The flow rate can be maintained at 1.0 ml per min. The peptide should elute and be free of serine and BTVS (hydrolyzed BTVSS).

Separate amino acid analyses of the HPLC fraction should show the peptide to contain one residue each of Thr, Val and two residues of Ser. The specific activity of both the serine recovered from amino acid analysis and that of the peptide should be the same on a molar basis.

EXAMPLE 11

TRANSPEPTIDATION WITH A TETRAPEPTIDE MODEL

This example illustrates the synthesis of the tetrapeptide Benzoyl-Gly-Ala-Pro-Phe-NH: from Benzoyl-Gly-Ala-Pro-Ala. About 10 μl of 100 mM of Benzoyl-Gly-Ala-Pro-Ala-OH (BGAPA) in dimethyl phthalate (DMP) may be combined with 19.11 μg/μl of 70 mM L-phenylalanine amide in 5 mM EDTA (pH 6.5). The reaction may be initiated by the addition of 15 μl of 22 mg/ml carboxypeptidase Y enzyme (CPD-Y). At preset time intervals, the reaction may be sampled by removing 10 μl aliquots and diluting with 200 μl of acetonitrile. Aliquots may be taken at the following approximate times: time 0 (prior to adding the enzyme), 1 minute, 5 minutes, 10 minutes, 20 minutes, 40 minutes, 1 hour, 2 hours, and 3 hours.

The samples may then be subjected to high pressure liquid chromatography (HPLC) using a reverse phase C-18 column developed with a linear gradient constructed from two solvents. A first solvent (A) can be 90% of 50 mM triethylamine phosphate (TEAP) (pH 3) with 10% acetonitrile, and the second solvent (B) can be 80% acetonitrile with 20% solvent A. TEAP may be prepared by titrating 50 mM phosphoric acid with distilled triethylamine to pH 3. A gradient can be developed over a 5 minute time period and can be initiated by mixing solvents A and B at the proportions of 1 part A and 0 part B and ended with 40 parts A and 60 parts B. The flow rate can be maintained at 1.5 ml per min. The BGAPA should disappear with the concommittant appearance of BGAPP-amide product and free alanine. The peptide should elute and be free of phenylalanine amide, BGAPA, and Ala.

Separate amino acid analyses of the HPLC fraction should show the peptide to contain one residue each of Benzoyl, Gly, Ala, Pro, and Phe. The specific activity of both the phenylalanine amide recovered from amino acid analysis and the phenylalanine amide in the peptide should be the same on a molar basis.

EXAMPLE 12

TRANSPEPTIDATION WITH ANTI-ASPARAGINE

SYNTHETASE MONOCLONAL ANTIBODY

This example illustrates the synthesis of C-Nor-C-($^{14}$C)Ser anti-asparagine synthetase monoclonal antibody (Nor-Mab-Ser*) from anti-asparagine synthetase monoclonal antibody (Mab). About 0.2 mM of Mab may be dissolved in 2 ml of 50 mM sodium carbonate buffer (pH 9.5) containing 1 mM EDTA and 0.25 M 14-C-serine. The reaction may be initiated by the addition of 5 μM of carboxypeptidase Y enzyme. At preset time intervals, the reaction may be sampled by removing 0.2 ml aliquots and diluting with 0.2 ml of acetonitrile, then adding 0.1 ml of 0.12 M acetic acid.

The samples may then be subjected to high pressure liquid chromatography (HPLC) using a reverse phase C-18 column developed with a linear gradient constructed from two solvents. A first solvent (A) can be 95% of 10 mM sodium acetate, 5% acetonitrile pH 4.5 and the second (B) can be 60% acetonitrile. A gradient can be developed over a 30 min time period and can be initiated by mixing solvents A and B at the proportions of 1 part A and 0 parts B and ended with 40 parts A and 60 parts B. The flow rate can be maintained at 1.0 ml per min. The Nor-Mab-Ser should elute and be free of serine and Mab. Separate amino acid analysis should show the Nor-Mab-Ser to contain one residue of Ser. The specific activity of both the serine recovered from amino acid analysis and that of the Nor-Mab-Ser* should be the same on a molar basis.

EXAMPLE 13

TRANSESTERIFICATION USING A TETRAPEPTIDE MODEL

This example illustrates the synthesis of Benzoyl-Thr-Val-Ser-(14 C)OMe from Benzoyl-Thr-Val-Ser-Ser. About 5 to 10 mM of Benzoyl-Thr-Val-Ser-Ser (BTVSS) may be dissolved in 2 ml of 50 mM sodium phosphate/phosphoric acid buffer (pH 3.5) containing 1 mM EDTA and 0.25 M $^{14}$C-methanol (MeOH). The reaction may be initiated by the addition of 5 μM of carboxypeptidase Y enzyme. At preset time intervals, the reaction may be sampled by removing 0.2 ml aliquots and diluting with 0.2 ml of acetonitrile, then adding 0.1 ml of 0.12 M acetic acid.

The samples may then be subjected to high pressure liquid chromatography (HPLC) using a reverse phase C-18 column developed with a linear gradient constructed from two solvents. A first solvent (A) can be 95% of 10 mM sodium acetate, 5% acetonitrile pH 4.5 and the second (B) can be 60% acetonitrile. A gradient can be developed over a 30 min time period and can be initiated by mixing solvents A and B at the proportions of 1 part A and 0 parts B and ended with 40 parts A and 60 parts B. The flow rate can be maintained at 1.0 ml per min.

The peptide should elute and be free of methanol and BTVS (hydrolyzed BTVSS}. Separate amino acid analysis should show the peptide to contain one residue each of Thr, Val and a Ser methyl ester. The specific activity of both the serine methyl ester recovered from amino acid analysis and that of the peptide should be the same on a molar basis.

EXAMPLE 14

TRANSESTERIFICATION USING ANTI-ASPARAGINE

SYNTHETASE MONOCLONAL ANTIBODY

This example illustrates the synthesis of $^{14}$C methyl C-nor-Anti-asparagine synthetase monoclonal antibody ester (*methyl-Nor-Mab) from anti-asparagine synthetase monoclonal antibody (Mab). About 0.2 mM of Mab may be dissolved in 2 ml of 50 mM sodium phosphate/-phosphoric acid buffer (pH 3.5) containing 1 mM EDTA and 0.25 M 14-C-Methanol. The reaction may be initiated by the addition of 5 μM of carboxypeptidase Y enzyme. At preset time intervals, the reaction may be sampled by removing 0.2 ml aliquots and diluting with 0.2 ml of acetonitrile, then adding 0.1 ml of 0.12 M acetic acid.

The samples may then be subjected to high pressure liquid chromatography (HPLC) using a reverse phase C-18 column developed column developed with a linear gradient constructed from two solvents. A first solvent (A) can be 95% of 10 mM sodium acetate, 5% acetonitrile pH 4.5 and the second (B) can be 60% acetonitrile. A gradient can be developed over a 30 min time period and can be initiated by mixing solvents A and B at the proportions of 1 part A and 0 parts B and ended with 40 parts A and 60 parts B. The flow rate can be maintained at 1.0 ml per min. The *methyl-Nor-Mab should elute and be free of methyl and Nor-Mab (hydrolyzed Mab). Separate amino acid analysis should show the *methyl-Nor-Mab to contain one residue of methyl serine ester. The specific activity of both the methyl serine ester recovered from amino acid analysis and that of the *methyl-Nor-Mab should be the same on a molar basis.

We claim:

1. A method for forming a protein bound to an auxiliary substance, comprising:

coupling a nucleophile to a protein having a C-terminus amino acid with the C-terminus as a carboxylic acid group, and an amino acid having a carbonyl group penultimate to the C-terminus amino acid by catalysis at acidic or basic pH with an exopeptidase enzyme to form an adduct, wherein the nucleophile is an amino acid derivative having an amine group and a side chain with a distinctive reactive substituent, and the coupling is between the amine group of the nucleophile and the C-terminus carboxylic acid group of the protein or the carbonyl group of the amino acid penultimate to the C-terminus of the protein; and, binding the adduct to the auxiliary substance or its combination with a linker arm to form the bound protein, wherein the auxiliary substance or combination has a specifically reactive group that is correlatively reactive toward the distinctive reactive substituent of the adduct, and the specifically reactive group and the distinctive reactive substituent react with each other without substantially involving other groups of the protein to accomplish the binding; and wherein the bound protein is a straight chain of the protein, nucleophile and auxiliary substance bonded together or a straight chain of the protein, nucleophile, linker and auxiliary substance bonded together, and only two sites on each of the nucleophile and linker as well as only one site on each of the protein and auxiliary substance are chain binding sites.

2. A method for forming a protein bound to an auxiliary substance, comprising:

binding a nucleophile to the auxiliary substance or its combination with a linker arm to form an intermediate, wherein the nucleophile is an amino acid derivative having an amine group or an alcohol group and with a reactive substituent and the auxiliary substance or combination has a reactive group that is reactive toward the reactive substituent of the nucleophile, and the binding is between the reactive substituent and the reactive group; and coupling the intermediate to a protein having a C-terminus amino acid with the C-terminus as a carbonylic acid group, and an amino acid having a carboxyl group penultimate to the C-terminus amino acid by catalysis at acidic or basic pH with an exopeptidase enzyme to form the bound protein, the coupling reaction being between the amine or alcohol group of the nucleophile within the intermediate and the C-terminus carboxylic acid group of the protein or the carbonyl group of the amino acid residue penultimate to the C-terminus of the protein; and wherein the bound protein is a straight chain of the protein, nucleophile and auxiliary substance bonded together or a straight chain of the protein, nucleophile, linker and auxiliary substance, and only two sites on each of the nucleophile and linker as well as only one site on each of the protein and auxiliary substance are chain binding sites.

3. A method for preparing a labeled protein, comprising:

coupling a nucleophile and a protein having a C-terminus amino acid with the C-terminus as a carboxylic acid group, and an 1) amino acid penultimate to the C-terminus amino acid having a carboxy group in a medium at acidic or basic pH and in the presence of an exopeptidase enzyme to form an adduct, said nucleophile being an amino acid, amino acid derivative, amine or 1) alcohol having an amine group or an alcohol group and a side chain with a distinctive reactive substituent selected from the group consisting of sulfhydryl, hydroxyl, activated hydroxyl, olefinyl, activated ester, amino, azidyl, hydrazinyl, phosphoramidoyl, boronyl, ferrocenyl, ferro complexes and mixtures thereof, wherein the concentration of said enzyme is from about 1 pM to 1 mM, and the coupling is between the amine or alcohol group of the nucleophile within the adduct and the C-terminus carboxylic acid group of the protein or the carbonyl group of the amino acid penultimate to the C-terminus of the protein;

combining a label and a linker arm to form a combination, said label being fluoroescent, nuclear magnetic, phosphorescent, colorimetric, magnetic, electron resonant or spectrometric and having at least one reactive group, said linker arm being a flexible or semi-flexible chain having a specifically reactive group that is correlatively reactive with the distinctive reactive substituent and another functional group that is reactive toward the reactive group of the label, and the combining being between the reactive group of the label and the functional group of the linker arm; and binding the adduct and the combination to form the labeled protein, the binding being between the distinctive reactive substituent and the specifically reactive group; wherein, the correlative reactivity of the specifically reactive group and the distinctive reactive substituent result in their reaction with each other without substantially involving other groups of the protein; and wherein the labeled protein is a straight chain of the protein, nucleophile, linker and label bonded together, and only two sites on each of the nucleophile and linker as well as only one site on each of the protein and label are chain binding sites.

4. A method for preparing a labeled protein, comprising:

combining a label and a linker arm to form a combination, said label being fluorescent, nuclear magnetic, phosphorescent, colorimetric or spectrometric and having at least one combining group, and said linker arm being a flexible or semi-flexible chain having a specifically reactive group that is or is rendered non-reactive with the combining group of the label and another functional group that is reactive toward the combining group of the label, and the combining is between the combining group of the label and the functional group of the linker arm;

binding the combination and a nucleophile to form an intermediate, said nucleophile being an amino acid, amino acid derivative, amine or alcohol having an amine group or an alcohol group and a side chain with a distinctive reactive substituent that is reactive toward the specifically reactive group of the combination, and the binding being between the distinctive reactive substituent and the specifically reactive group; and coupling the intermediate and a protein having a C-terminus amino acid having a carbonyl group with the C-terminus as a carboxylic acid group, and an amino acid penultimate to the C-terminus amino acid in a medium at acidic or basic pH and in the presence of an exopeptidase enzyme to form the labeled protein, wherein the concentration of the enzyme is from about 1 pM to 1 mM, and the coupling is between the amino or alcohol group of the nucleophile within the intermediate and the C-terminus carboxylic acid group of the protein or the carbonyl group of the amino acid penultimate to the C-terminus of the protein; and wherein the labeled protein is a straight chain of the protein, nucleophile, linker and label bonded together, and only two sites on each of the nucleophile and linker as well as only one site on each of the protein and label are chain binding sites.

5. A method according to claim 3 or 4 wherein the coupling conditions are basic and the nucleophile is an amino acid, amino acid derivative or amine, and the reaction is conducted for at least about 5 seconds.

6. A method according to claim 3 or 4 wherein the protein, nucleophile and enzyme are combined in an aqueous mixture, wherein the aqueous mixture is formed by:

(a) combining the protein and the nucleophile to form a mixture;

(b) adjusting the pH of the mixture to within a range of about 2.0 to 10.5; and (c) adding the enzyme to the mixture.

7. A method according to claim 3 or 4 wherein the reaction between the distinctive reactive substituent and the specifically reactive group is a non-competitive reaction which does not involve other functional groups of the protein or a competitive reaction which is controlled to provide substantially selective reaction between the specifically reactive group and distinctive reactive substituent relative to the reaction of either of the specifically reactive group and the distinctive reactive substituent with other functional groups of the protein.

* * * * *